(12) United States Patent
Park et al.

(10) Patent No.: US 12,336,931 B2
(45) Date of Patent: Jun. 24, 2025

(54) ORAL COOLING DEVICE UTILIZING COOLING BALLOON

(71) Applicant: THE CATHOLIC UNIVERSITY OF KOREA INDUSTRY-ACADEMIC COOPERATION FOUNDATION, Seoul (KR)

(72) Inventors: Sung Soo Park, Seoul (KR); Byung Hee Hwang, Seoul (KR); Chang Ki Min, Seoul (KR); Jong Hyuk Lee, Seoul (KR)

(73) Assignee: THE CATHOLIC UNIVERSITY OF KOREA INDUSTRY-ACADEMIC COOPERATION FOUNDATION, Seoul (KR)

( * ) Notice: Subject to any disclaimer, the term of this patent is extended or adjusted under 35 U.S.C. 154(b) by 885 days.

(21) Appl. No.: 17/265,411

(22) PCT Filed: Sep. 21, 2020

(86) PCT No.: PCT/KR2020/012701
§ 371 (c)(1),
(2) Date: Feb. 2, 2021

(87) PCT Pub. No.: WO2021/085858
PCT Pub. Date: May 6, 2021

(65) Prior Publication Data
US 2022/0110787 A1    Apr. 14, 2022

(30) Foreign Application Priority Data
Oct. 30, 2019   (KR) .................. 10-2019-0136648

(51) Int. Cl.
*A61F 7/00* (2006.01)
*A61F 7/12* (2006.01)

(52) U.S. Cl.
CPC ............ *A61F 7/123* (2013.01); *A61F 7/0085* (2013.01); *A61F 2007/0017* (2013.01); *A61F 2007/0056* (2013.01); *A61F 2007/0092* (2013.01)

(58) Field of Classification Search
CPC .................. A61F 7/123; A61F 7/0085; A61F 2007/0017; A61F 2007/0056;
(Continued)

(56) References Cited

U.S. PATENT DOCUMENTS 5,509,801 A * 4/1996 Nicholson ............ A61C 19/06
601/165
6,796,972 B1 * 9/2004 Sinofsky ............... A61M 25/04
604/93.01

(Continued)

FOREIGN PATENT DOCUMENTS

JP         4871256 B2    2/2012
JP     2012530554 A  * 12/2012
(Continued)

*Primary Examiner* — Adam Z Minchella
*Assistant Examiner* — Ashleigh Lauren Kern
(74) *Attorney, Agent, or Firm* — Bridgeway IP Law Group, PLLC; Jihun Kim

(57) ABSTRACT

Proposed is an oral cooling device using a cooling balloon, including: a cooling water supply portion provided with a cooler that cools cooling water and a pump that supplies and recovers the cooling water; a cooling water hose portion connected to the cooling water supply portion to transfer the supplied cooling water and recover the recovered cooling water to the cooling water supply portion; and a cooling balloon portion which is connected to an end portion of the cooling water hose portion, expands by the supplied cooling water to cool an inside of an oral cavity of a patient after
(Continued)

being inserted into a mouth of the patient, and contracts in a case where the cooling water is recovered to the cooling water supply portion.

8 Claims, 3 Drawing Sheets

(58) Field of Classification Search
CPC ........ A61F 2007/0092; A61F 2007/022; A61F 2007/0268; A61F 7/12; A61F 7/10; A61F 2007/0287

See application file for complete search history.

(56) References Cited

U.S. PATENT DOCUMENTS

| | | | | |
|---|---|---|---|---|
| 8,888,832 | B2* | 11/2014 | Lim | A61F 7/123 |
| | | | | 607/105 |
| 2002/0183692 | A1* | 12/2002 | Callister | A61F 7/123 |
| | | | | 604/113 |
| 2005/0209662 | A1* | 9/2005 | Lunderqvist | A61F 7/123 |
| | | | | 607/113 |
| 2006/0276552 | A1* | 12/2006 | Barbut | A61M 25/0032 |
| | | | | 514/743 |
| 2018/0140407 | A1* | 5/2018 | Yoskowitz | A61C 19/08 |
| 2018/0338787 | A1* | 11/2018 | Cote | A61B 90/98 |

FOREIGN PATENT DOCUMENTS

| | | | |
|---|---|---|---|
| KR | 20170051444 A | * | 5/2017 |
| KR | 2018-0132106 A | | 12/2018 |

* cited by examiner

ORAL COOLING DEVICE UTILIZING COOLING BALLOON

TECHNICAL FIELD

The present invention relates to an oral cooling device, and more particularly, an oral cooling device utilizing a cooling balloon, which prevents the occurrence of oral mucositis by cooling the mucosal tissue in the oral cavity by injecting cooling water into a balloon placed in the mouth to expand the balloon and bringing the mucosal tissue in the oral cavity and the balloon to contact with each other.

BACKGROUND ART

An anticancer drug is essential for the treatment of cancer patients. For example, in the case of multiple myeloma (a type of blood cancer), a high dose of melphalan anticancer drug is administered for an autologous stem-cell transplantation treatment, and in this case, severe mucositis occurs in most patients due to the toxicity of melphalan.

Severe oral mucositis that occurs in this way causes infection by passing damaged bacteria in the oral cavity through the mucosa, and also causes the disorder of food intake through the oral cavity, which results in not only the need for intravenous nutrition therapy (nutrient infusion), but also the deterioration of all morbid conditions such as an extension of the length of hospital stay.

Therefore, treatments and prophylactic methods for preventing or reducing oral mucositis caused by the toxicity of anticancer drugs in cancer patients treated with anticancer drugs are still being actively studied. As an example, there is a research result that an oral cooling therapy in which gargling is performed with ice cubes in the oral cavity during the period in which an anticancer drug is injected can reduce oral mucositis. Cancer patients (multiple myeloma mentioned above) treated with an oral cooling treatment using ice before and after the administration of melphalan had a statistically significant reduction in the oral mucositis of severity grade of 3 or higher, the duration of administration of an analgesic, and the duration of intravenous administration of nutrition compared to the control group who had been gargled with only saline solution.

This is based on the fact that the oral cooling therapy induces constriction of blood vessels in the oral mucosa and thus reduces a blood flow rate in the oral mucosa, thereby minimizing the exposure of anticancer drugs to the oral mucosa.

However, although it is ideal to commercialize an icemaker or a water purifier for ice making for such an oral cooling therapy to be regularly and repeatedly applied to patients, in a treatment field, the demand for sanitary verification and management of ice-making products as well as disinfection and single-use replacement of internally manufactured filters is essential. Therefore, it was not easy to develop and apply such products universally.

Hygiene guarantee is a value criterion that absolutely reflects the specificity of medical auxiliary devices, and it would be the most hygienic to prepare a cooling agent using disposable devices. However, there are no oral cooling induction products that can be commercialized and utilized until now. Accordingly, for an oral cooling treatment, skilled medical personnel have to manually manufacture and supply ice for oral cooling. In particular, the problem of labor consumption caused a problem in the clinical practice field in that a relatively long period of time (65 minutes in the case of melphalan, an anticancer drug) was required, and it was not easy to utilize the oral cooling treatment despite its expected excellent effect. From the perspective of a patient receiving an oral cooling treatment, the patient has to repeat for a long period of time a process of repeatedly putting the provided ice in the mouth for a predetermined period of time, gargling while melting the ice, and spitting the ice out again, causing discomfort in access to treatment.

In order to solve these problems, improved treatment technologies were required to easily perform oral cooling therapy, and according to these requirements, "a mouthpiece cooling the oral tissue of a patient during chemotherapy treatment" of Korean Patent Application Publication No. 2018-0132106, which is manufactured in the form of a mouthpiece and creates a cooling environment by reducing the capillary blood flow, and an intraoral cooling device such as "a mouth cooler" of Korean Patent Application Publication No. 2017-0051444, which includes a cooling winding and cools the mouth by bringing fusible cooling flaps that are inserted into the mouth in the form of a mouthpiece into contact with the upper and lower jaw, and the upper and lower parts and sides of the tongue, and the like, have been provided.

However, in the case of the above-described intraoral cooling devices in the related art, due to the fixed frame structure such as a mouthpiece, the devices have to be customized for individual patients, resulting in a problem that universal use cannot be achieved. In addition, cleaning and disinfection are not easy, so that there is a high risk of potential infection.

CITATION LIST

Korean Patent Application Publication No. 2018-0132106
Korean Patent Application Publication No. 2017-0051444

SUMMARY OF INVENTION

Technical Problem

Therefore, the present invention is to solve the problems of the related art described above, and an object thereof is to develop an intraoral cooling device which can be used universally without restrictions to patients, maximize hygiene by facilitating cleaning and disinfection, and provide an efficient cooling effect inside the oral cavity.

Solution to Problem

In order to achieve the above object, according to an embodiment of the present invention, there is provided an oral cooling device using a cooling balloon, including: a cooling water supply portion configured with a cooler that cools cooling water and a pump that supplies and recovers the cooling water; a cooling water hose portion connected to the cooling water supply portion to transfer the supplied cooling water and recover the recovered cooling water to the cooling water supply portion; and a cooling balloon portion which is connected to an end portion of the cooling water hose portion, expands by the supplied cooling water to cool an inside of an oral cavity of a patient after being inserted into a mouth of the patient, and contracts in a case where the cooling water is recovered to the cooling water supply portion.

The cooling water supply portion is configured to include: a cooling water tank that stores the cooling water recovered after being supplied to the cooling balloon portion; and a cooler attached to the cooling water tank to cool the cooling water stored in the cooling water tank.

The cooling water tank is configured to include: a partition wall which is provided at a center of the cooling water tank and divides an inside of the cooling water tank into a supply tank and a recovery tank which lower portions communicate with each other; a supply pipe formed to cause an inside and an outside of the supply tank to communicate with each other so as to enable the cooling water of the supply tank to be discharged to the outside; a supply pump attached to the supply pipe so as to provide a supply pressure for supplying the cooling water to the outside; a recovery pipe through which the cooling water from the outside is recovered to the recovery tank; and a recovery pump attached to the recovery pipe to provide a recovery pressure for introducing the cooling water from the outside into the recovery tank.

The oral cooling device further includes: a connection pipe portion having one end portion attachable to and detachable from the cooling water hose portion and the other end portion detachably connected to the cooling balloon portion.

The connection pipe portion is configured to include: a fixed pipe having one end portion to which the cooling water hose portion is connected; and a cooling balloon portion connection pipe formed to connect the cooling balloon portion to the other end portion of the fixed pipe.

The cooling water hose portion is configured to include: a cooling water supply hose through which the cooling water is transferred to the cooling balloon portion; and a cooling water recovery hose through which the cooling water of the cooling balloon portion is transferred to the cooling water supply portion.

The fixed pipe is configured to include a supply hose connection pipe to which the cooling water supply hose is connected and a recovery hose connection pipe to which the cooling water recovery hose is connected in one end portion.

An inside of one or more of the supply hose connection pipe and the recovery hose connection pipe is provided with a backflow prevention portion for preventing a backflow of the cooling water.

In the connection pipe portion, the fixed pipe and the cooling balloon portion connection pipe are separated, and the connection pipe portion is configured to further include: a bearing member that rotatably insert and connect the cooling balloon portion connection pipe to the fixed pipe; and a rotational driving portion that rotates the cooling balloon portion connection pipe relative to the fixed pipe.

The cooling balloon portion is configured to include one or more cooling balloons branching into branches.

The oral cooling device using a cooling balloon further includes: a controller portion which performs control of cooling of the cooling water of the cooling water tank, supply of the cooling water, recovery of the cooling water, and rotational driving of the cooling balloon portion.

The controller portion is configured to perform control such that the cooling water is supplied to the cooling balloon portion, the cooling water supplied to the cooling balloon portion is recovered to the cooling water supply portion after a predetermined period of time elapses, and then the cooling balloon portion is rotated at a predetermined angle relative to the connection pipe portion.

Advantageous Effects of Invention

In the above-described embodiment of the present invention, the oral cooling device using a cooling balloon can be used universally without restrictions to specific patients, maximizes hygiene guarantee and reduces the risk of potential infection by facilitating cleaning and disinfection, and provides an efficient oral cavity cooling effect.

In addition, while existing ice gargling has a problem of potential infection because ice in an ice making process is exposed to the air in a freezer and in an atmosphere before being applied to a patient, in the oral cooling device using a cooling balloon in the embodiment of the present invention, the cooling water is not exposed to the outside, so the occurrence of contamination is fundamentally blocked. In addition, the cooling water supply portion, the cooling water hose portion, the connection pipe portion, and the cooling balloon portion can be separated to be cleaned and disinfected, so personalized hygiene is provided for patients receiving a treatment such as anticancer therapy in which a hygienic environment is essential, and an effect of minimizing potential concerns about infectious diseases is provided.

In addition, the oral cooling device using a cooling balloon in the embodiment of the present invention eliminates a manual production and a freezing procedure of a cooling agent by medical personnel compared to an existing ice gargling method. Therefore, the ability to provide oral cooling therapy is significantly improved, the manpower, cost, and time required are minimized, thereby providing an effect of significantly reducing medical expenses.

In addition, the oral cooling device using a cooling balloon in the embodiment of the present invention does not require the patient to frequently bite and spit ice for a certain period of time compared to the case of performing the existing ice gargling method, thereby providing an effect of significantly improving the convenience of the patient performing the oral cooling therapy.

DESCRIPTION OF EMBODIMENTS

Figure 1:
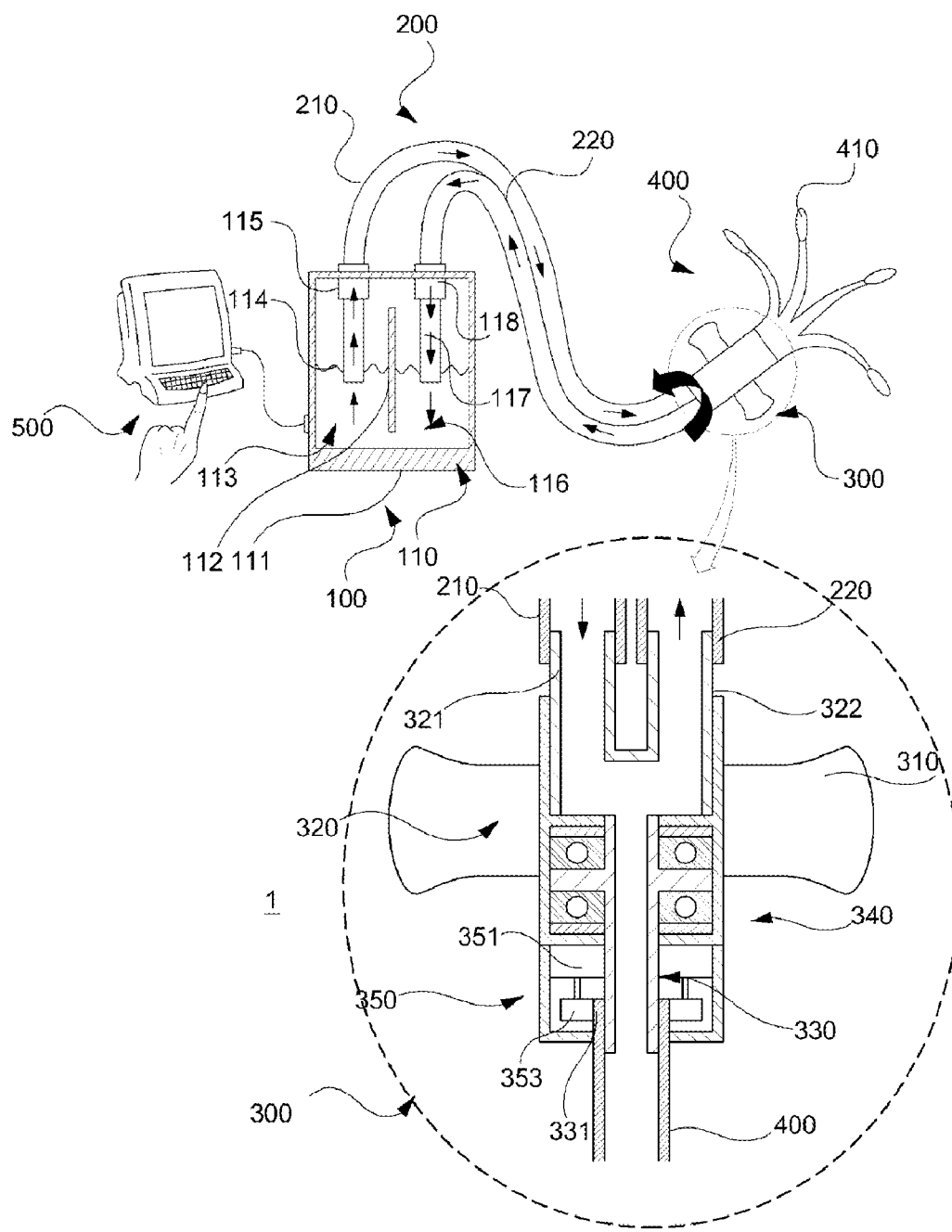
FIG. 1 is a configuration diagram of an oral cooling device utilizing a cooling balloon according to an embodiment of the present invention.

In the following description of the present invention, in a case where it is determined that a detailed description of a related known function or configuration may unnecessarily obscure the gist of the present invention, the detailed description will be omitted.

Since the embodiments according to the concept of the present invention can apply various changes and have various forms, specific embodiments will be illustrated in the drawings and described in detail in the present specification or application. However, this is not intended to limit the embodiments according to the concept of the present invention to a specific form of disclosure, and the present invention should be understood to include all changes, equivalents, and substitutes included in the spirit and scope of the present invention.

When a component is referred to as being "connected" or "linked" to another component, it should be understood that it may be directly connected or linked to the other component, or another component may also be present therebetween. On the other hand, when a component is referred to as being "directly connected" or "directly linked" to another component, it should be understood that there is no other component therebetween. Other expressions describing the relationship between components, such as "between" and "just between" or "adjacent to" and "directly adjacent to" should be construed similarly.

The terms used in the present specification are only used to describe specific embodiments, and are not intended to limit the present invention. Singular expressions include plural expressions unless the context clearly indicates otherwise. In the present specification, terms such as "include" or "have" are intended to designate the presence of instructed features, numbers, stages, operations, components, parts, and combinations thereof, and have to be understood that the presence or possibility of addition of one or more other features or combinations thereof is not excluded in advance.

In an embodiment of the present invention, there is provided an oral cooling device using a cooling balloon, including: a cooling water supply portion provided with a cooler that cools cooling water and a pump that supplies and recovers the cooling water; a cooling water hose portion connected to the cooling water supply portion to transfer the supplied cooling water and recover the recovered cooling water to the cooling water supply portion; and a cooling balloon portion which is connected to an end portion of the cooling water hose portion, expands by the supplied cooling water to cool an inside of an oral cavity of a patient after being inserted into a mouth of the patient, and contracts in a case where the cooling water is recovered to the cooling water supply portion.

The cooling water supply portion may be configured to include: a cooling water tank that stores the cooling water recovered after being supplied to the cooling balloon portion; and a cooler attached to the cooling water tank to cool the cooling water stored in the cooling water tank.

The cooling water tank may be configured to include: a partition wall which is provided at a center of the cooling water tank and divides an inside of the cooling water tank into a supply tank and a recovery tank which lower portions communicate with each other; a supply pipe formed to cause an inside and an outside of the supply tank to communicate with each other so as to enable the cooling water of the supply tank to be discharged to the outside; a supply pump attached to the supply pipe so as to provide a supply pressure for supplying the cooling water to the outside; a recovery pipe through which the cooling water from the outside is recovered to the recovery tank; and a recovery pump attached to the recovery pipe to provide a recovery pressure for introducing the cooling water from the outside into the recovery tank.

The oral cooling device may further include: a connection pipe portion having one end portion detachably connected to the cooling water hose portion and the other end portion detachably connected to the cooling balloon portion.

The connection pipe portion may be configured to include: a fixed pipe having one end portion to which the cooling water hose portion is connected; and a cooling balloon portion connection pipe formed to connect the cooling balloon portion to the other end portion of the fixed pipe.

The cooling water hose portion may be configured to include: a cooling water supply hose through which the cooling water is transferred to the cooling balloon portion; and a cooling water recovery hose through which the cooling water of the cooling balloon portion is transferred to the cooling water supply portion, and the fixed pipe may be configured to include a supply hose connection pipe to which the cooling water supply hose is connected and a recovery hose connection pipe to which the cooling water recovery hose is connected in one end portion.

An inside of one or more of the supply hose connection pipe and the recovery hose connection pipe may be provided with a backflow prevention portion for preventing a backflow of the cooling water.

In the connection pipe portion, the fixed pipe and the cooling balloon portion connection pipe may be separated, and the connection pipe portion may be configured to further include: a bearing member that rotatably insert and connect the cooling balloon portion connection pipe to the fixed pipe; and a rotational driving portion that rotates the cooling balloon portion connection pipe relative to the fixed pipe.

The cooling balloon portion may be configured to include one or more cooling balloons branching into branches.

The oral cooling device using a cooling balloon may further include: a controller portion which performs control of cooling of the cooling water of the cooling water tank, supply of the cooling water, recovery of the cooling water, and rotational driving of the cooling balloon portion.

The controller portion may be configured to perform control such that the cooling water is supplied to the cooling balloon portion, the cooling water supplied to the cooling balloon portion is recovered to the cooling water supply portion after a predetermined period of time elapses, and the cooling balloon portion is rotated at a predetermined angle relative to the connection pipe portion.

Hereinafter, the present invention will be described in more detail with reference to the accompanying drawings showing embodiments of the present invention.

FIG. 1 is a configuration diagram of an oral cooling device utilizing a cooling balloon according to an embodiment of the present invention.

As illustrated in FIG. 1, the oral cooling device utilizing a cooling balloon of the embodiment of the present invention may be configured to include: a cooling water supply portion 100 provided with a cooler 111 that cools cooling water and a pump 115 or 118 that supplies and recovers the cooling water; a cooling water hose portion 200 connected to the cooling water supply portion 100 to transfer the supplied cooling water and recover the recovered cooling water to the cooling water supply portion 100; and a cooling balloon portion 400 that is connected to an end portion of the cooling water hose portion 200, expands by the supplied cooling water to cool the inside of the oral cavity of a patient after being placed in the mouth of the patient, and contracts in a case where the cooling water is recovered to the cooling water supply portion.

In the above configuration, the cooling water supply portion 100 may be configured to include a cooling water tank 110 that stores the cooling water recovered after being supplied to the cooling balloon portion, and a cooler 111 attached to the cooling water tank 110 to cool the cooling water stored in the cooling water tank 110.

At this time, the cooling water tank 110 may be configured to separate the cooling water to be supplied and the recovered cooling water so that a temperature rise due to mixing of the cooling water that has been cooled to a predetermined temperature or lower so as to be supplied to the cooling balloon portion 400 and the cooling water recovered from the cooling balloon portion 400 is minimized.

For this, the cooling water tank 110 may be configured to include a partition wall 112 at the center, which divides the inside into a supply tank 113 and a recovery tank 116 of which lower portions communicate with each other.

The supply tank 113 may be configured to include a supply pipe 114 formed to cause the inside and the outside of the supply tank 113 to communicate with each other so as to enable the cooling water of the supply tank 113 to be discharged to the outside, and a supply pump 115 attached to the supply pipe so as to provide a supply pressure for supplying the cooling water to the outside.

The recovery tank 116 may be configured to include a recovery pipe 117 through which the cooling water from the outside is recovered to the recovery tank, and a recovery pump 118 attached to the recovery pipe 117 to provide a recovery pressure for introducing the cooling water from the outside into the recovery tank.

The supply pump 115 and the recovery pump 118 may be configured to be driven directly by a user, or may be configured to be controlled to be driven by a controller portion 500 to be described below.

In this case, the cooling water hose portion 200 may be configured as a single tube, or may be configured to be separated into a cooling water supply hose 210 through which the cooling water is transferred to the cooling balloon portion 400 and a cooling water recovery hose 220 through which the cooling water of the cooling balloon portion 400 is recovered to the cooling water supply portion 100.

In addition, the oral cooling device 1 utilizing a cooling balloon according to the embodiment of the present invention may be configured to further include a connection pipe portion 300 that detachably connects the cooling water hose portion 200 and the cooling balloon portion 400 to each other so that cleaning, disinfection, and the like of the supply hose portion 200 and the cooling balloon portion 400 can be easily performed.

The connection pipe portion 300 may be configured to include a fixed pipe 320 having one end portion to which the cooling water hose portion 200 is connected, and a cooling balloon portion connection pipe 330 formed to connect the cooling balloon portion 400 to the other end portion of the fixed pipe 320.

The fixed pipe 320 and the cooling balloon portion connection pipe 330 may be formed integrally with each other, but may also be configured separately for rotational driving of the cooling balloon portion 400.

In a case where the connection pipe portion 300 is configured such that the fixed pipe 320 and the cooling balloon portion connection pipe 330 are separated for the rotational driving of the cooling balloon portion 400, the connection pipe portion 300 may be configured to further include the fixed pipe 320, the cooling balloon portion connection pipe 330, and a bearing member 340 which rotatably insert and connect the cooling balloon portion connection pipe 330 to the fixed pipe.

In addition, the connection pipe portion 300 may be configured to further include a rotational driving portion 350 that rotates the cooling balloon portion connection pipe 330 relative to the fixed pipe so that the cooling balloon portion connection pipe 330 can be rotated at regular intervals. The rotational driving portion 350 may be configured to include a driving motor 351 in which a cooling balloon portion gear 331 formed on the outer surface of the cooling balloon portion connection pipe 330 and a motor gear 353 are axially connected to each other. In this case, the driving motor 351 performs an operation of rotating the cooling balloon portion 400 at a predetermined angle in the oral cavity by being driven to rotate under the control of the controller portion 500. In addition to the above-described motor method, the rotational driving portion 350 may be variously embodied such as in a configuration in which the rotational driving portion 350 has one end portion rotatably connected to the cooling water supply portion 100, extends through the cooling water hose portion 200, and has the other end portion connected to the cooling balloon portion connection pipe 330 to rotate the cooling balloon connection pipe 330.

In addition, the connection pipe portion 300 may be configured to further include a mouthpiece 310 connected to the outside of the fixed pipe 320 in order to enable the patient to bite and fix the connection pipe portion 300.

The cooling balloon portion 400 may be configured to have one cooling balloon, and may be configured to include a plurality of cooling balloons 410 branched into branches to separately cool the mucous membranes inside the oral cavity.

In addition, the oral cooling device 1 of the present invention may be configured to further include the controller portion 500 which performs control of the cooling of the cooling water of the cooling water tank 110, supply of the cooling water, recovery of the cooling water, and the rotational driving of the cooling balloon portion 400.

In this case, the controller portion 500 may be configured to include a display device and control buttons on the outside, and a control unit (not illustrated) that controls the driving of the cooling water supply portion 100 and the connection pipe portion 300 on the inside.

At this time, the control unit may be configured to perform control such that the supply pump 115 is driven to supply the cooling water to the cooling balloon portion 400, the recovery pump 118 is driven to recover the cooling water supplied to the cooling balloon portion 400 to the cooling water supply portion 100 after a predetermined period of time elapses, and thereafter the rotational driving portion 350 is controlled to rotate the cooling balloon portion 400 at a predetermined angle relative to the connection pipe portion 300 so as to rotate the cooling balloon portion connection pipe 330 at a predetermined angle relative to the fixed pipe 320.

Figure 2:
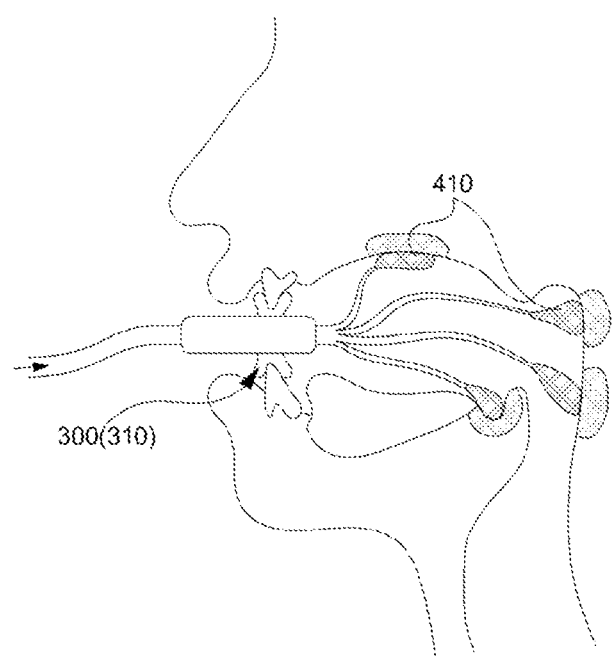
FIG. 2 is a view of a state in which the cooling balloon into which cooling water is injected for cooling the inside of the oral cavity is expanded and an oral cooling therapy is being performed.
Figure 3:
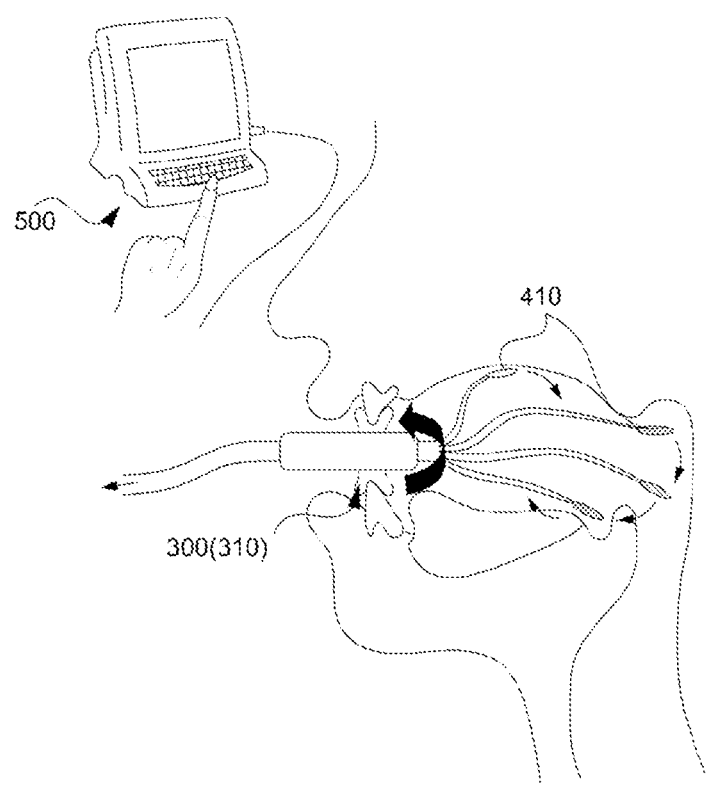
FIG. 3 is a view illustrating a process of rotating a cooling balloon portion to change a cooling position after discharging the cooling water of the cooling balloon.

FIG. 2 is a view of a state in which the cooling balloon into which the cooling water is injected for cooling the inside of the oral cavity is expanded and an oral cooling therapy is being performed, and FIG. 3 is a view illustrating a process of rotating the cooling balloon portion to change a cooling position after discharging the cooling water of the cooling balloon.

In a case where an oral cooling therapy is performed during a treatment such as an anticancer drug treatment, if necessary, the cooler 111 is driven to cool the cooling water stored in the cooling water tank 110, or to maintain the driven state of the cooler during the treatment.

Thereafter, in a state where the cooling balloon portion 400 is placed in the oral cavity of the patient and bitten and fixed by the patient, the cooling water is supplied to the cooling balloon portion 400 by driving the supply pump 115 through direct control by the user or through the controller portion 500 in a case where the controller portion 500 is provided, such that the cooling balloons 410 expand. The expanded cooling balloons 410 are brought into contact with cooling treatment sites inside the oral cavity of the patient and perform a cooling treatment.

Thereafter, after a predetermined period of time elapses, the supply pump 115 is stopped through direct control by the user or through the controller portion 500 in the case where the controller portion 500 is provided, and then the recovery pump 118 is driven to recover the cooling water of the cooling balloon portion 400 to the cooling water supply portion 100.

By repeatedly performing the process of supplying and recovering the cooling water for a certain period of time, the oral cooling treatment of the patient is performed.

At this time, in a case where the cooling balloon portion connection pipe 330 is configured to be rotated relative to the fixed pipe 320, after recovering the cooling water of the cooling balloon portion 400, the cooling balloon portion 400 is rotated inside the oral cavity through the direct control by the user or the control of the rotation by the rotational driving portion 350, whereby the positions of the cooling balloons 410 can be changed and the oral cooling therapy can be performed on other mucous membrane areas in the oral cavity.

While the technical spirit of the present invention described above has been specifically described in the preferred embodiment, it should be noted that the embodiment is for the purpose of description and not for the limitation thereof. In addition, those skilled in the technical field of the present invention will understand that various embodiments are possible within the scope of the technical spirit of the present invention. Therefore, the true technical protection scope of the present invention should be determined by the technical spirit of the appended claims.

REFERENCE SIGNS LIST

1: Cooling balloon oral cooling device
100: Cooling water supply portion
110: Cooling water tank
111: Cooler
112: Partition wall
113: Supply tank
114: Supply pipe
115: Supply pump
116: Recovery tank
117: Recovery pipe
118: Recovery pump
200: Cooling water hose portion
210: Cooling water supply hose
220: Cooling water recovery hose
300: Connection pipe portion
310: Mouthpiece
320: Fixed pipe
321: Supply hose connection pipe
322: Recovery hose connection pipe
330: Cooling balloon portion connection pipe
331: Cooling balloon portion gear
340: Bearing member
350: Rotational driving portion
351: Motor
353: Motor gear
400: Cooling balloon portion
410: Cooling balloon
500: Controller portion

The invention claimed is:

1. An oral cooling device using a cooling balloon, the oral cooling device comprising:
a cooling water supply portion having therein a cooler that is configured to cool cooling water and a pump that is configured to supply and recover the cooling water;
a cooling water hose portion connected to the cooling water supply portion at one end portion of the cooling water hose portion to transfer the cooling water and recover the cooling water to the cooling water supply portion;
a cooling balloon portion configured to expand by the cooling water to cool an inside of an oral cavity of a patient after being inserted into a mouth of the patient, the cooling balloon portion being configured to contract when the cooling water is recovered to the cooling water supply portion, the cooling balloon portion branching into a plurality of branches, a distal end of each of the plurality of branches having a balloon attached thereto to separately cool a plurality of mucosal areas inside the oral cavity; and
a connection pipe portion,
wherein the connection pipe portion includes:
a fixed pipe having one end detachably connected to the cooling water hose portion;
a cooling balloon portion connection pipe having one end detachably and rotatably connected to another end of the fixed pipe, another end of the cooling balloon portion connection pipe being detachably connected to the cooling balloon portion, the cooling balloon portion connection pipe having a cooling balloon portion gear on an outer surface thereof;
a mouthpiece disposed on an outer surface of the fixed pipe and configured to enable the patient to bite and fix the fixed pipe; and
a rotational driving portion disposed on the outer surface of the cooling balloon portion connection pipe, the rotational driving portion having a motor gear axially engaged with the cooling balloon portion gear,
wherein the rotational driving portion is configured to rotate the cooling balloon portion connection pipe relative to the fixed pipe while the fixed pipe remains stationary when the patient bites the mouthpiece, such that the cooling balloon portion connected to the cooling balloon portion connection pipe rotates about an axial direction of the fixed pipe by a predetermined angle within the mouth of the patient.

2. The oral cooling device using the cooling balloon according to claim 1,
wherein the cooling water supply portion further includes:
a cooling water tank configured to store the cooling water,
wherein the cooler is attached to the cooling water tank to cool the cooling water stored in the cooling water tank.

3. The oral cooling device using the cooling balloon according to claim 1,
wherein the cooling water supply portion includes:
a partition wall disposed at a center of the cooling water supply portion and dividing an inside of the cooling water supply portion into a supply tank and a recovery tank, wherein the partition wall is open at lower portions of the supply tank and the recovery tank, such that the supply tank and the recovery tank are communicating with each other at the lower portions;
a supply pipe configured to connect an inside of the supply tank to the cooling water hose portion to enable the cooling water of the supply tank to be discharged to the cooling water hose portion;
a supply pump attached to the supply pipe to provide a supply pressure for supplying the cooling water to the cooling water hose portion;
a recovery pipe configured to recover the cooling water from the cooling water hose portion to the recovery tank; and a recovery pump attached to the recovery pipe to provide a recovery pressure for introducing the cooling water from the cooling balloon portion into the recovery tank.

4. The oral cooling device using the cooling balloon according to claim 3, further comprising:
a controller configured to perform control of cooling of the cooling water of the cooling water supply portion, suppling of the cooling water, recovering of the cooling water, and rotational driving of the cooling balloon portion.

5. The oral cooling device using the cooling balloon according to claim 4,
wherein the controller is configured to, in a sequential order, control the supply pipe to supply the cooling water to the cooling balloon portion, control the recovery pipe to recover the cooling water supplied to the cooling balloon portion to the cooling water supply portion after a predetermined period of time, control the rotational driving portion to rotate the cooling balloon portion at a predetermined angle relative to the connection pipe portion, and control the supply pipe to re-supply the cooling water to the cooling balloon portion that is rotated.

6. The oral cooling device using the cooling balloon according to claim 1,
wherein the cooling water hose portion includes:
a cooling water supply hose configured to transfer the cooling water therethrough to the cooling balloon portion; and
a cooling water recovery hose configured to transfer the cooling water from the cooling balloon portion therethrough to the cooling water supply portion, and
wherein the fixed pipe includes a supply hose connection pipe configured to be connected to the cooling water supply hose and a recovery hose connection pipe configured to be connected to the cooling water recovery hose at one end portion.

7. The oral cooling device using the cooling balloon according to claim 6,
wherein at least one of an inside of the supply hose connection pipe and an inside of the recovery hose connection pipe has a backflow prevention portion configured to prevent a backflow of the cooling water.

8. The oral cooling device using the cooling balloon according to claim 1,
wherein the connection pipe portion further includes:
a bearing configured to rotatably insert and connect the cooling balloon portion connection pipe to the fixed pipe.

* * * * *